United States Patent [19]

Lea, Jr. et al.

[11] 3,990,253

[45] Nov. 9, 1976

[54] METHOD FOR CONSTRUCTING AN ICE PLATFORM

[75] Inventors: James F. Lea, Jr.; Joseph E. Zupanick, both of Richardson, Tex.

[73] Assignee: Sun Oil Company (Delaware), Dallas, Tex.

[22] Filed: June 19, 1975

[21] Appl. No.: 588,253

[52] U.S. Cl. .................................. 61/103; 61/53; 62/260; 165/45
[51] Int. Cl.² ...................... E02D 5/22; E02B 17/00
[58] Field of Search............. 61/46, 1 R, 53, 36 A, 61/46.5; 166/DIG. 1; 62/260; 165/45

[56] References Cited
UNITED STATES PATENTS

| | | | |
|---|---|---|---|
| 3,732,918 | 5/1973 | Culbertson | 61/1 R |
| 3,750,412 | 8/1973 | Fitch et al. | 61/46 |
| 3,798,912 | 3/1974 | Best et al. | 61/46 |

*Primary Examiner*—Paul R. Gilliam
*Assistant Examiner*—Alex Grosz
*Attorney, Agent, or Firm*—J. Edward Hess; Donald R. Johnson; William C. Roch

[57] ABSTRACT

A work platform for oil drilling, oil production, or other purposes is constructed in arctic waters by locating a natural ice island of suitable area and thickness, and moving it to the desired platform location. The ice island is anchored to the sea floor by installing at least one, but preferably a number of, generally cylindrical sheaths beneath it which extend from the island to the sea floor below. The sheaths are filled with water, and a thermosiphon is installed interiorly of the sheath. As the thermosiphon extracts heat from the water within the sheath, the water is converted to ice, and eventually the entire body of water within the sheath is frozen, thereby forming a column of ice which anchors the island to the sea floor in the desired location.

8 Claims, 3 Drawing Figures

METHOD FOR CONSTRUCTING AN ICE PLATFORM

BACKGROUND OF THE INVENTION

The conduct of off-shore oil and gas drilling and production operations in shallow arctic waters is a more formidable engineering task than off-shore operations in temperate areas because of the continuing threat presented to the drilling platform or production platform by pack ice and ice floes characteristic of the arctic waters.

In addition to pack ice and ice floes, ice islands are fairly common in arctic water. These are pieces of ice thought to originate on continental land masses, and may be of considerable area, as well as greater in average thickness than a typical sheet of pack ice. These ice islands, as well as pieces of pack ice of sufficient area and thickness, offer the possibility of being utilized as ice platforms for drilling and other operations if they can be secured in the desired location in a manner adequate to give them sufficient sturdiness and stability against the tendencies of ocean currents and wind, as well as moving pack ice and ice floes to move them out of position. Up to the present, no feasible method or means has been available for this purpose.

SUMMARY OF THE INVENTION

In accordance with the present invention, a method is provided for constructing an ice platform in arctic waters of sufficient sturdiness to be usable for drilling, production, and other industrial or scientific operations. First, an ice island, or a sheet of pack ice, of sufficient area and thickness to serve as a suitable work platform is located among the natural ice formations in the arctic waters, and is moved by the use of tugs or otherwise to the desired location for the platform. If necessary, the piece of ice for use as a platform may be cut or broken away from a larger section of ice. Next, the process of affixing the piece of ice to the ocean floor is carried out by positioning a thin, generally cylindrical sheath beneath the ice platform. At least one such sheath should be employed, and it is preferred to utilize a number of them. The sheath may be installed in various ways, but it is preferred to drill a hole in the piece of ice having a diameter slightly larger than that of the sheath, and to drill a similar hole in the sea floor below the piece of ice. The sheath is preferably installed so that it penetrates the sea floor for some distance, and also extends upwardly into the interior of the piece of ice. The sheath is then filled with water, either seawater which flows in through one or more relatively small openings in the sheath, or through the bottom as the sheath is installed, or with seawater or fresh water pumped in through the open top of the sheath. The purpose of the sheath is to substantially enclose a body of water and maintain it in quiescent condition, as compared to the flowing condition of the surrounding seawater, where ocean currents are at work, during the next step in the method.

Next, one or more thermosiphons are installed in the interior of the sheath. These operate to extract heat from the water within the sheath, and a column of ice starts to grow around the body of the siphon. As the siphon continues to withdraw heat from the water within the sheath, the column of ice grows until it occupies the entire interior of the sheath, as well as the hole which has been bored in the ocean floor, and the hole which was bored in the piece of ice. There is thereby created a column of ice which is integral with the ice of the platform itself, and which extends into the sea floor a selected distance. This column of ice serves to anchor the ice platform in the desired location, and to give it resistance against the pressures exerted by ocean currents, by the wind, and by ice packs and ice floes driven by wind and current.

From the foregoing, it can be seen that the principal object of the present invention is the provision of a method for constructing and/or maintaining a work platform in an arctic environment formed of ice. Other objects and purposes, together with this object, may be more fully understood from a consideration of the detailed description which follows, taken together with the accompanying drawings.

DESCRIPTION OF THE PREFERRED EMBODIMENT

Figure 1:
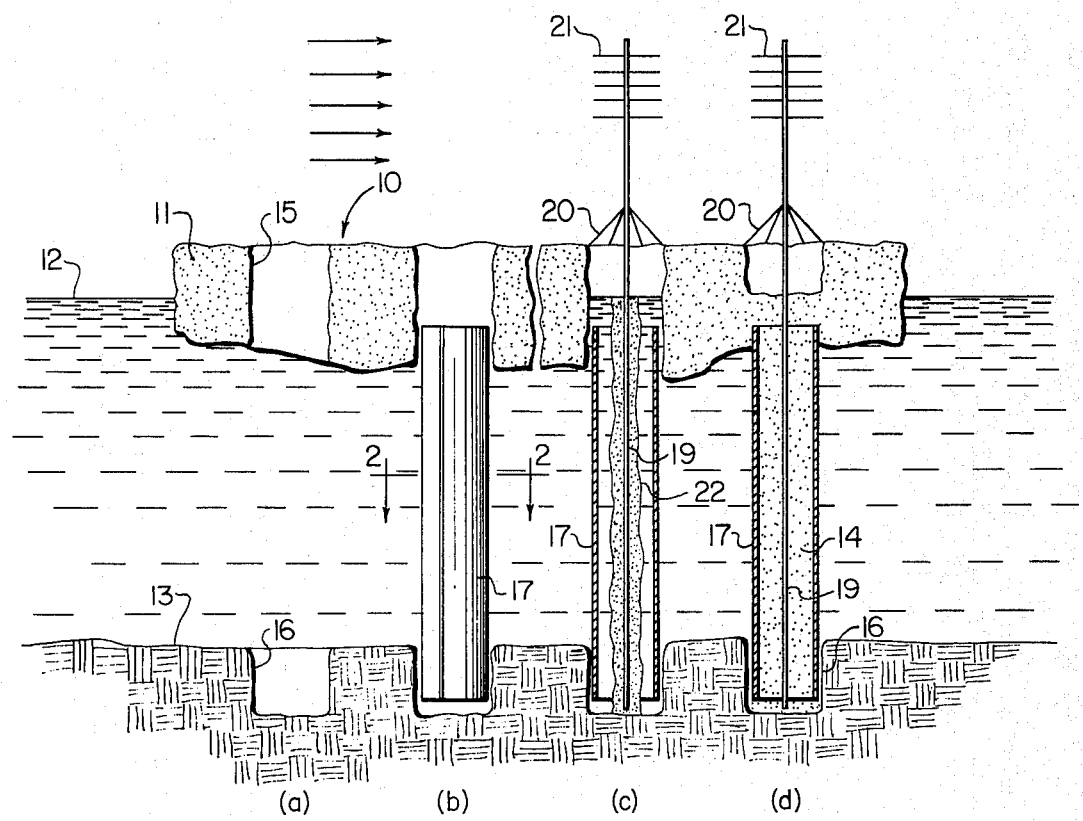
FIG. 1 is a cross-sectional elevational diagrammatic view of an ice platform constructed in accordance with the method of the invention, illustrating several different steps involved in the practice of the method.

Attention is first directed to FIG. 1, which shows in diagrammatic form the practice of the invention. In FIG. 1 the ice platform constructed in accordance with the invention is designated generally as 10. Platform 10 comprises ice sheet 11, which is afloat in sea 12 above sea floor 13, and is connected to the sea floor by one or more ice columns 14. The ice platform 10 may be located in water between about 20 feet and about 60 feet in depth.

FIG. 1 is drawn to illustrate four stages in the installation of an ice column 14, and the four sections of the figure are labeled, from left to right, (a), (b), (c), and (d), for convenience in discussion.

In stage (a), a hole 15 has been cut in ice sheet 11, after the sheet has been positioned in the desired location for an ice column. A hole of substantially the same diameter has been bored in the sea floor 13 directly below hole 15. The sea floor hole is designated 16 in FIG. 1.

Figure 2:
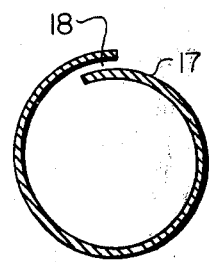
FIG. 2 is a plan cross-sectional view taken along the line 2—2 of FIG. 1, and illustrating a sheath employed in accordance with the invention.

In stage (b), a thin, generally cylindrical sheath 17 has been installed so that it fits at one end at least partly into sea floor hole 16, and at the upper end at least partly into hole 15 in sheet of ice 11. Sheath 17 is adapted to be filled with water, either seawater or fresh water, and several forms of construction may be employed to so adapt it. A preferred form of construction is illustrated in the cross-sectional view of FIG. 2. As there shown, sheath 17 is formed of sheet metal rolled into a generally cylindrical configuration, with an overlap at the edges of the sheath forming a narrow slot 18. When the sheath 17 is installed as is illustrated in section (b) of FIG. 1, seawater can flow into the interior of the sheath through slot 18, thereby filling the interior with water. However, slot 18 is small enough so that the body of water within sheath 17 is quiescent, and substantially uninfluenced by sea currents. Other means for accomplishing the purpose of establishing within the sheath 17 a body of quiescent water may be employed. For example, sheath 17 may be perforated at selected locations. Still another alternative is to employ a sheath which is substantially watertight along its length, and to fill it by pumping or siphoning from the top with seawater or fresh water, or by allowing water to flow in the bottom as the sheath is lowered into position.

Sheath 17 is sized to provide desired structural strength in the system consisting of sea floor 13, sheath 17 (destined to become ice column 14), and ice sheet 11. Typically, a sheath one to five feet in diameter may be employed.

The next stage in the construction of ice platform 10 is illustrated in part (c) of FIG. 1. As can be seen there, a thermosiphon 19 is installed in the interior of sheath 17. Mounting struts 20 for the thermosiphon 19 are provided at the surface of ice sheet 11. Thermosiphon 19 is provided with heat exchange fins 21 at its top in order to increase the efficiency of heat transfer between the upper end of the siphon and the cold arctic atmosphere. Thermosiphons are known devices, whose structure and operation are discussed below in connection with FIG. 3. At this point, it is sufficient to point out that thermosiphon 19 extracts heat from the quiescent body of water inside sheath 17 and transfers that heat to the ambient arctic air. As it does so, a column of ice 22 forms around siphon 19.

Although only a single thermosiphon 19 is shown installed in sheath 17 in part (c) of FIG. 1, it should be understood that several parallel thermosiphons may be installed if it is so desired. In such event, a plurality of ice columns 22 will grow within sheath 17, one centered upon each of the thermosiphons. In any event, ice column 22 will grow, in the course of time, until it completely fills the interior of sheath 17.

Part (d) of FIG. 1 shows the completed ice column 14 within protective sheath 17. From part (d) it can be seen that ice column 14 is integral with ice sheet 11 at the top, and penetrates into the sea floor 13 to substantially fill the hole 16, which has been bored in the sea floor. Thermosiphon 19 is preferably left in place upon completion of the column 14 to maintain it in frozen condition, notwithstanding the presence of warmer seawater surrounding the ice column. On those days when the ambient temperature is such that the thermosiphon will tend to pump heat into the ice column 14 instead of pumping it out of the column, an insulating boot may be placed over heat transfer fins 21 at the upper end of the siphon to substantially retard such undesirable heat flow.

Figure 3:
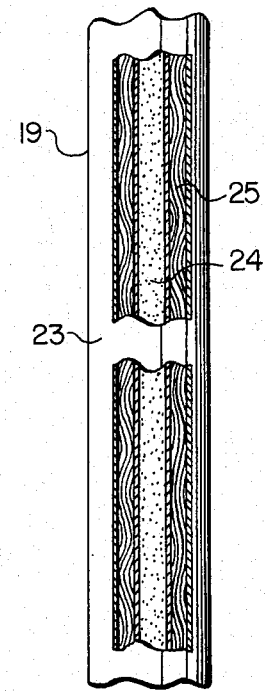
FIG. 3 is a diagrammatic fragmentary elevational view, with some parts broken out, of a thermosiphon of the kind employed in the practice of the method of the invention.

Attention is now directed to FIG. 3, which illustrates in somewhat diagrammatic form the structure and operation of a thermosiphon 19. In FIG. 3, the middle section of the siphon is shown broken away, and portions of the outer container are broken out to reveal the interior structure. Thermosiphon 19 comprises a generally cylindrical housing 23 within which is a central bore 24, preferably surrounded by porous wicking material 25. A quantity of heat exchange fluid is contained within the housing 23. Various heat exchange fluids may be employed; the fluid selected should be one that boils at a temperature somewhat below the freezing point of water, and condenses at a temperature well above the winter ambient arctic temperature. Examples of suitable heat exchange fluids are ammonia, freon-12, and propane. In the lower portion of thermosiphon 19, heat supplied by the surrounding water within sheath 17 is absorbed by the heat exchange fluid, which vaporizes and flows upwardly in bore 24. At the upper end of the siphon, the exchange vapor gives up its heat of vaporization to the ambient atmosphere, the flow of such heat being aided by fins 21 (see FIG. 1), and condenses. The condensed heat exchange fluid then flows by capillary action downwardly through wick material 25 to the lower portion of the siphon or by gravity if no wick is provided. Thermosiphons are known per se, and are described in various portions of the literature. For a simplified discussion of them, see the article entitled "Heat Pipes — New Ways to Transfer Energy" by Edelson appearing in the June 1974 issue of *Popular Science* at pages 102 et seq.

From the foregoing, it can be seen that in accordance with the present invention, a simple and practical method of constructing an ice platform in arctic waters is provided.

What is claimed is:

1. A method for constructing an ice platform in arctic waters comprising:
   a. positioning a naturally formed ice sheet of suitable area and thickness at the desired location of the platform;
   b. installing at least one protective sheath beneath the ice sheet, coupled to said ice sheet, extending to and being supported by the sea floor;
   c. establishing a body of quiescent water within said sheath; and
   d. extracting heat from said body of quiescent water to thereby freeze the quiescent water in the protective sheath into an ice column integral with said ice sheet.

2. A method in accordance with claim 1 in which a thermosiphon is employed for said heat extraction.

3. A method in accordance with claim 1 in which said sheath extends into the sea floor.

4. A method in accordance with claim 1 in which said sheath extends into said ice sheet.

5. A method in accordance with claim 1 in which said sheath is pervious to the surrounding seawater and said body of quiescent water is established by inflow of seawater.

6. A method in accordance with claim 1 in which said sheath is impervious to the surrounding seawater and said body of quiescent water is established by flowing water into an end of said sheath.

7. A method in accordance with claim 2 in which a plurality of thermosiphons is employed.

8. A method in accordance with claim 5 in which said sheath comprises a generally cylindrical sheet with lapping edges.

* * * * *